United States Patent
Jutras et al.

(10) Patent No.: US 7,274,958 B2
(45) Date of Patent: Sep. 25, 2007

(54) REGISTRATION POINTER WITH INTERCHANGEABLE TIP AND METHOD

(75) Inventors: Sébastien Jutras, Montréal (CA); Herbert Jansen, Montréal (CA); Louis-Philippe Amiot, Montréal (CA)

(73) Assignee: Orthosoft Inc., Montréal (CA)

( * ) Notice: Subject to any disclaimer, the term of this patent is extended or adjusted under 35 U.S.C. 154(b) by 922 days.

(21) Appl. No.: 10/263,772

(22) Filed: Oct. 4, 2002

(65) Prior Publication Data

US 2004/0068179 A1   Apr. 8, 2004

(51) Int. Cl.
*A61B 5/05* (2006.01)
(52) U.S. Cl. .................... 600/429; 600/424; 606/130
(58) Field of Classification Search ............... 600/424, 600/429; 606/130
See application file for complete search history.

(56) References Cited

U.S. PATENT DOCUMENTS

| | | | | |
|---|---|---|---|---|
| 6,021,343 | A * | 2/2000 | Foley et al. ............... | 600/429 |
| 6,430,434 | B1 * | 8/2002 | Mittelstadt ................. | 600/426 |
| 2003/0153829 | A1 * | 8/2003 | Sarin et al. ................ | 600/426 |
| 2005/0059885 | A1 * | 3/2005 | Melkent et al. ............. | 600/424 |

FOREIGN PATENT DOCUMENTS

WO   WO 01/67979 A1   9/2001

OTHER PUBLICATIONS

U.S. Appl. No. 60/403,642, not published, Jansen.

* cited by examiner

*Primary Examiner*—Brian L. Casler
*Assistant Examiner*—John F. Ramirez
(74) *Attorney, Agent, or Firm*—Ogilvy Renault LLP (57) ABSTRACT

A registration pointer for registering points of surfaces of bodily elements in computer-assisted surgery, comprising a handle for being manipulated by a pointer operator. A stem is connected to the handle and has a first and a second tip configurations each having a respective use relating to a registration of points on specified bodily elements. A detectable device is secured to the stem, and is adapted to be tracked in space for position and orientation by a sensing apparatus. A position of the tip configurations with respect to the detectable device is determinable such that a position of the tip configurations is calculable as a function of the position and orientation of the detectable device. The tip configurations are chosen to register points on given bodily elements as a function of the respective use, by recording a position of points of contact between the tip configurations and the given bodily element.

15 Claims, 5 Drawing Sheets

REGISTRATION POINTER WITH INTERCHANGEABLE TIP AND METHOD

FIELD OF THE INVENTION

The present invention generally relates to registration pointers used in computer-assisted surgery (CAS) and, more particularly, to a registration pointer having an interchangeable tip enabling various uses of the registration pointer.

BACKGROUND OF THE INVENTION

In CAS systems, registration pointers are used in combination with trackable reference systems to digitize points of bodily elements for various purposes, such as obtaining 3D models of bones. A registration pointer is typically trackable in a working field of the CAS system, and is calibrated such that the position of a tip thereof is known as a function of the tracking thereof by the CAS system. The tip of the registration pointer contacts a surface to be digitized, and a registration command or operation from a surgeon will have the point of contact between the tip of the registration pointer and the surface registered.

Registration pointers have evolved so as to be provided with additional features. As an example, some types of pointers are provided with a pointed tip that can be used to perform perforations in soft tissue. Such a pointed tip not only reduces the invasiveness of the registration process of CAS, but also accelerates the surgical procedures by removing the step of performing a pre-registration incision. Such an additional feature is in line with important design factors of CAS: reduce the invasiveness of surgery, and accelerate surgical procedures. These design factors must be applied to all aspects of the registration pointers, including sterilization and calibration.

However, a problematic issue with pointed-tip registration pointers is that pointed tips can perforate organs and canals. For instance, in some orthopaedic CAS procedures such as hip replacement, registration points are frequently taken on the pelvis. For registration points taken on the pubic tubercle, there is a risk of perforating the urethra.

SUMMARY OF THE INVENTION

It is therefore an aim of the present invention to provide a registration pointer having interchangeable tips for respective uses on given bodily element surfaces in computer-assisted surgery.

It is a further aim of the present invention to provide a system having a registration pointer with interchangeable tips.

It is a still further aim of the present invention to provide a method for registering points with the registration pointer of the present invention.

It is a still further aim of the present invention to provide a calibration method for the registration pointer of the present invention so as to simplify calibration.

It is a still further aspect of the present invention to provide a single registration pointer having more than one use to simplify sterilization and inventory.

Therefore, in accordance with the present invention, there is provided a registration pointer for registering points of surfaces of bodily elements in computer-assisted surgery, comprising a handle for being manipulated by a pointer operator; at least first and second tip configurations each having a respective use relating to a registration of points on specified bodily elements; at least one stem for connecting at least one of the first and the second tip configurations to the handle; and a detectable device secured to any one of the handle and the tip configurations, the detectable device being adapted to be tracked in space for position and orientation by a sensing apparatus; whereby a position of any one of the tip configurations with respect to the detectable device is determinable such that a position of any one of the tip configurations is calculable as a function of the position and orientation of the detectable device, any one of the tip configurations being chosen to register points on given bodily elements as a function of the respective use, by recording a position of points of contact between any one of the tip configurations and the given bodily element.

Further in accordance with the present invention, there is provided a system for registering points on surfaces of bodily elements in computer-assisted surgery, comprising a registration pointer having a first and a second tip configurations each having a respective use relating to a registration of points on specified bodily elements, and a detectable device trackable in space for position and orientation, any one of the tip configurations being chosen to register points on given bodily elements as a function of the respective uses; a sensing apparatus for tracking a position and orientation of the detectable device; and a position calculator connected to the sensing apparatus, for calculating a position of any one of the tip configurations of the registration pointer as a function of the position and orientation of the detectable device provided by the sensing apparatus, the position calculator being adapted to register points on surfaces of bodily elements by recording a position of points of contact between any one of the tip configurations and the bodily elements.

Still further in accordance with the present invention, there is provided A method for registering points on surfaces of bodily elements in computer-assisted surgery, comprising the steps of i) providing a registration pointer with at least a first and a second tip configurations each having a respective use relating to a registration of points on specified bodily elements, and being trackable in space for position and orientation; ii) calibrating the registration pointer such that a position in space of any one of the tip configurations is calculable by a position calculator as a function of the tracking for position and orientation of the registration pointer; iii) registering points on a surface of a first bodily element with the first tip configuration by recording a position of points of contact between the first tip configuration and the surface of the first bodily element; iv) indicating to the position calculator a change of use from the first tip configuration to the second tip configuration for the registration pointer; and v) registering points on a surface of a second bodily element with the second tip configuration by recording a position of points of contact between the second tip configuration and the surface of the second bodily element.

BRIEF DESCRIPTION OF THE DRAWINGS

Having thus generally described the nature of the invention, reference will now be made to the accompanying drawings, showing by way of illustration a preferred embodiment thereof and in which.

DESCRIPTION OF THE PREFERRED EMBODIMENTS

Figures 1, 2:
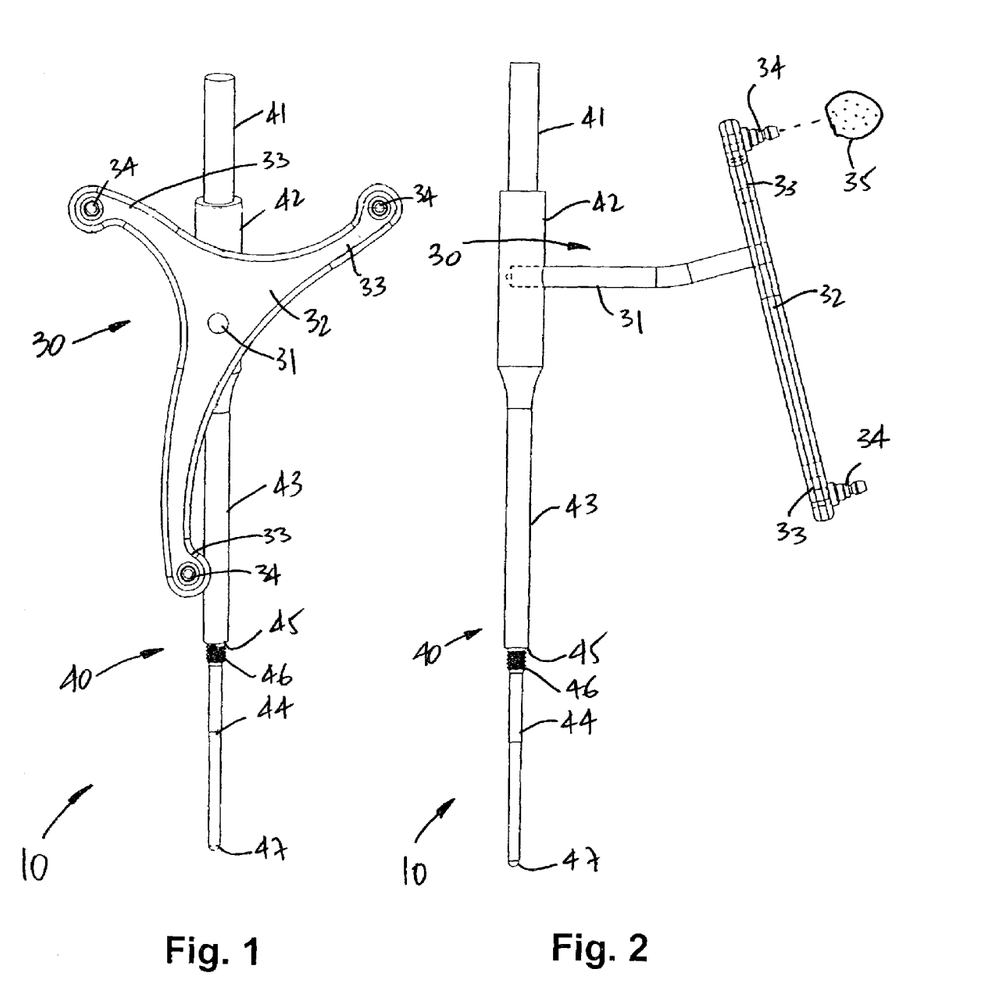
FIG. 1 is a perspective view of a registration pointer in a hemispherical tip configuration in accordance with the present invention.
FIG. 2 is an elevation view of the registration pointer in the hemispherical tip configuration.
Figure 3:
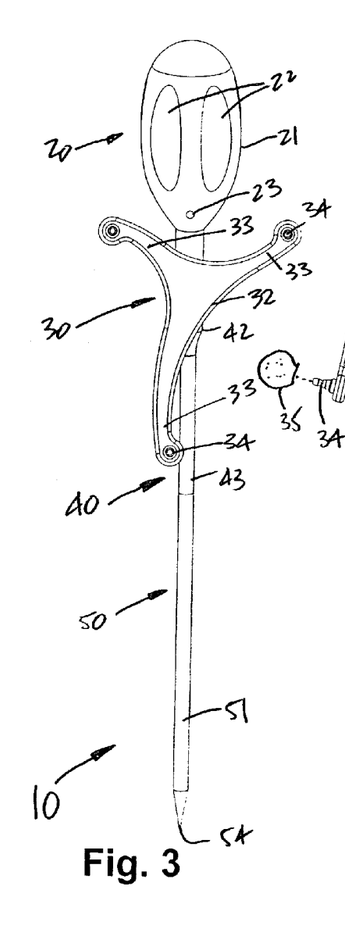
FIG. 3 is a perspective view of the registration pointer in a pointed tip configuration in accordance with the present invention.
Figure 4:
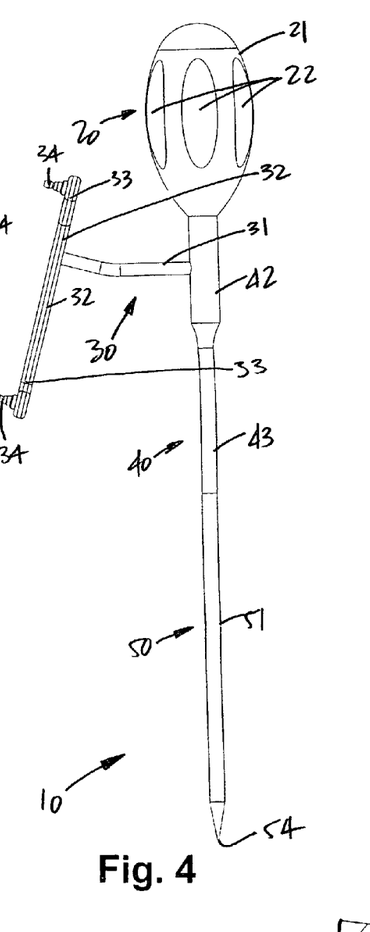
FIG. 4 is an elevation view of the registration pointer in the pointed tip configuration.
Figure 5:
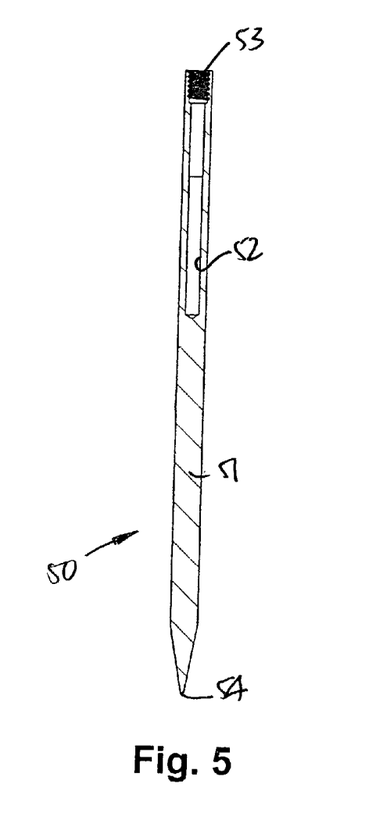
FIG. 5 is a cross-sectional longitudinal view of a removable tip of the pointed tip configuration of the registration pointer.

Referring to the drawings, and more particularly to FIG. 1, a registration pointer in accordance with the present invention is generally shown at 10. The registration pointer 10 has a handle portion 20 (FIGS. 3 and 4), a detectable device base 30, a stem portion 40, and, as shown in FIGS. 3 to 5, a removable tip 50. In FIGS. 3 and 4, the removable tip 50 is shown secured to the stem portion 40 of the registration pointer 10 in a second tip configuration (also referred to as pointed tip configuration for the shape of the tip). The first tip configuration (also referred to as hemispherical tip configuration for the shape of the tip) is illustrated in FIGS. 1 and 2, wherein the removable tip 50 is not on the stem portion 40. In FIG. 5, the removable tip 50 is shown separately, having been removed from the registration pointer 10.

Referring to FIGS. 3 and 4, components of the handle portion 20 are illustrated bearing reference numerals in the twenties. It is pointed out that the handle portion 20 has been separated from the other components of the registration pointer 10 in FIGS. 1 and 2, to illustrate the interconnection between the handle portion 20 and the stem portion 40. The handle portion 20 has a body 21, generally having the outline of a teardrop, as shown in FIG. 4. A plurality of gripping concavities 22 are provided on a peripheral surface of the body 21. The concavities 22 will facilitate the handling of the registration pointer 10, as fingertips of a pointer operator can be nested therein. The body 21 consists of a sterilizable material, providing appropriate friction for ease of manipulation. The body 21 is secured to the stem portion 40 by mating engagement therewith. For instance, the body 21 can be force-fitted onto the stem portion 40, with a pin 23 (FIG. 4) ensuring the engagement therebetween. The pin 23 is blended into the peripheral surface of the body 21, such that the peripheral surface remains smooth.

Referring to FIGS. 1 to 4, components of the detectable device base 30 are illustrated bearing reference numerals in the thirties. The detectable device base 30, hereinafter base 30, has an arm 31 protruding radially from the stem portion 40. A support plate 32 is secured to a free end of the arm 31, and has three fingers 33, each having a snap-fit pin 34. The snap-fit pins 34 are adapted to receive detectable devices thereon in snap-fitting engagement, such as retro-reflective spheres, one of which is illustrated at 35. The three fingers 33 are in a predetermined pattern, so as to be recognized by a CAS system for tracking for position and orientation, as will be explained in detail hereinafter. It has been thought to provide the detectable device base 30 with a passive interface. For instance, U.S. provisional patent application No. 60/403,462 by Jansen, entitled "Interface Apparatus for Passive Tracking Systems and Method of Use Thereof", filed on Aug. 16, 2002, describes suitable passive references, whereby the specification thereof is incorporated herein by reference.

As seen in FIG. 2, the arm 31 has a portion thereof received in a corresponding bore in the stem portion 40. The arm 31 is preferably welded to the stem portion 40. The arm 31 is slightly bent to orient the support plate 32 so as to be visible by the CAS system.

Referring to FIGS. 1 and 2, the stem portion 40 is illustrated in the first tip configuration of the registration pointer 10. Components of the stem portion 40 will bear reference numerals in the forties. The stem portion 40 has a generally circular cross-section, and is connected to the handle portion 20 by end 41. A support portion 42 of the stem portion 40 has an enlarged diameter with respect to other portions of the stem portion 40, as the support portion 42 is bored to support the base 30.

An intermediate portion 43 of the stem portion 40 is positioned between the support portion 42 and a tip portion 44. The tip portion 44 has a smaller diameter than the intermediate portion 43, thereby creating a shoulder 45. Threading 46 is provided on the peripheral surface of the tip portion 44 adjacent to the shoulder 45. A tip 47 of the tip portion 44 has a hemispherical shape.

Figure 6:
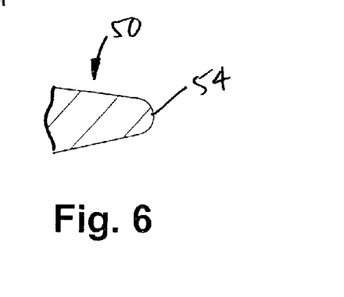
FIG. 6 is an enlarged fragmented view of a tip of the removable tip of the pointed tip configuration of the registration pointer.

Referring to FIG. 5, components of the removable tip 50 are shown bearing reference numerals in the fifties. The removable tip 50 has an elongated hollow body 51 having an inner cavity 52. The inner cavity 52 has tapping 53 adjacent to an opening thereof. A tip 54 of the removable tip 50 has a pointed shape. As shown in FIG. 6, the very end of the tip 54 can have a hemispherical shape.

FIGS. 3 and 4 illustrate the registration pointer 10 in the second tip configuration, wherein the removable tip 50 is secured to the stem portion 40. More precisely, the removable tip 50 covers the tip portion 44 of the stem portion 40, with the respective tapping 53 and threading 46 operatively cooperating to secure the pieces together. The removable tip 50 abuts the shoulder 45. Accordingly, the inner cavity 52 has a circular cross-section, similar to the tip portion 44, and is deep enough for receiving the tip portion 44. The tolerance between the periphery of the tip portion 44 and the surface of the inner cavity 52 is such that the tip portion 44 and the removable portion 50 in the second tip configuration are coaxial. Also, the outer diameter of both the intermediate portion 43 and the removable portion 50 is the same such that an outer surface of the registration pointer 10 in the second tip configuration is smooth and continuous. Threading engagement is described for securing the removable tip 50 to the stem portion 40. However, other fastening means are contemplated, such as any type of quick coupling including snap-fit connector/socket, pin and slot, and the like.

Referring to FIGS. 1 and 2, the tip portion 44 is illustrated having a portion thereof adjacent to the threading 46 having a slightly greater diameter than an end portion thereof. On the other hand, as illustrated in FIG. 5, the removable tip 50 has a portion of the inner cavity 52 adjacent to the tapping 53 having a slightly smaller diameter than deeper portions of the inner cavity 52. These diameters are provided to have a precise fit of the tip portion 44 in the inner cavity 52 of the removable tip 50, to ensure a proper co-axial alignment between the stem portion 40 and the removable tip 50 engaged thereon. The greater diameter portion of the tip portion 44 and the smaller diameter portion of the inner cavity 52 are opposed when the removable tip 50 is screwed to the stem portion 40. Obviously, this fit could have been reproduced on the full length of the tip portion 44 and throughout the depth of the inner cavity 52, but the above described construction involves smaller machining costs.

Referring to FIGS. 1 and 2, the first tip configuration, i.e., the registration pointer 10 without the removable tip 50, is specified for invasive uses. The tip 47 has a hemispherical shape such that it can be probed through soft tissue, without causing substantial damage thereto, to find and register bone element. For instance, the tip 47 can be used to register points on the pelvic tubercles with low risks of perforating canals or organs, such as the urethra. It is pointed out that the reduced diameter of the tip portion 44 is another parameter that will limit the damage caused to the soft tissue.

Referring to FIGS. 3 and 4, the second tip configuration, i.e., the registration pointer 10 having the removable tip 50 matingly covering the tip portion 44, is specified for registering bone element reference points on thin soft tissue. For instance, a few bodily parts have a soft tissue layer covering the bone element: the malleoli, the iliac crests, the epicondyles, etc. It is desired, in an effort to reduce the invasiveness of surgery, to register points of the bone element directly on the soft tissue. Accordingly, the removable tip 50 is well suited for such use. The tip 54 is pointed to minimize the amount of soft tissue between the registration pointer 10 and the bone element, yet it has a hemispherical shape (FIG. 6) to avoid perforating the soft tissue.

Figures 9, 10:
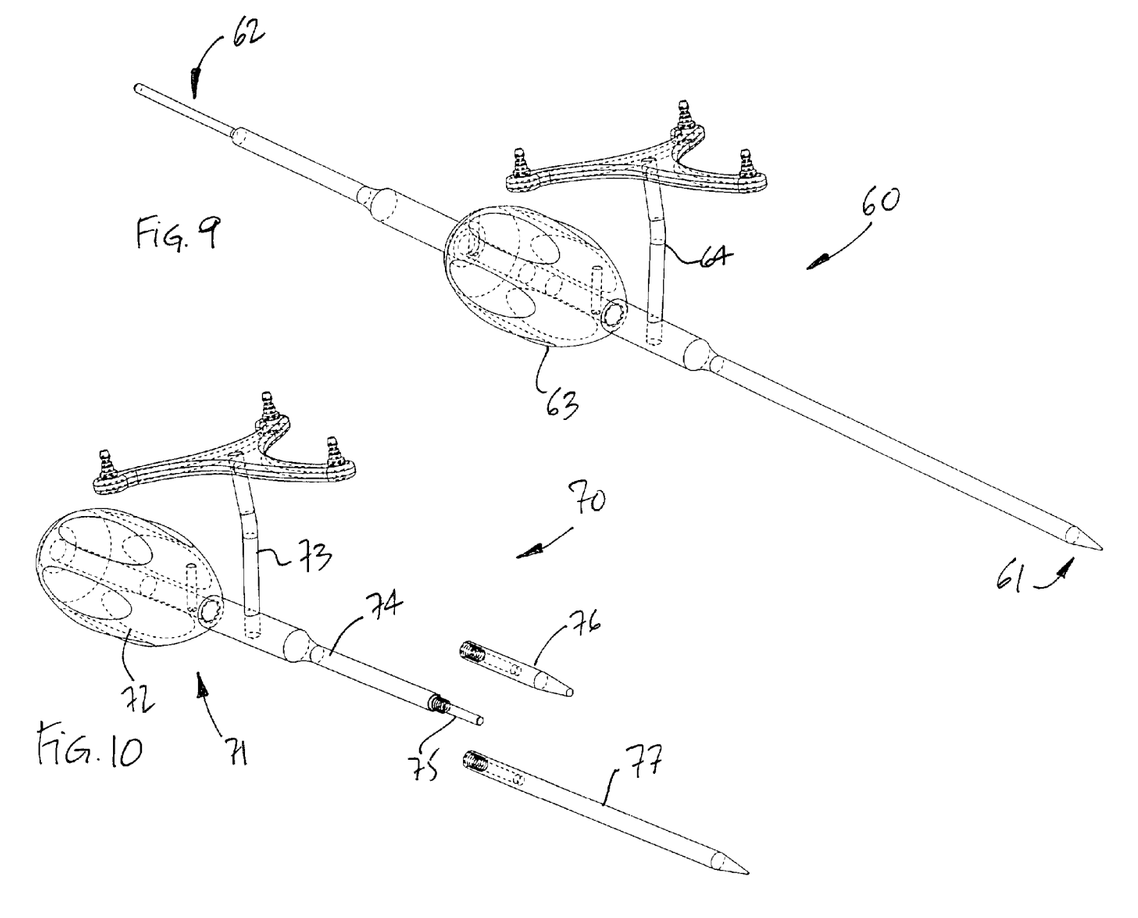
FIG. 9 is a perspective view of the registration pointer having a pair of tip configurations integrally formed therewith in accordance with a further embodiment of the present invention.
FIG. 10 is a perspective view of the registration pointer having a base body and bit-type tip configurations in accordance with a still further embodiment of the present invention.

As illustrated in FIGS. 9 and 10, other tip configurations are contemplated. Referring to FIG. 9, a registration pointer in accordance with another embodiment of the present invention is illustrated at 60. The registration pointer 60 is provided with a pair of tip configurations 61 and 62 integrally part of the registration pointer 10 and projecting from opposed ends of a handle portion 63, with the tip configurations 61 and 62 having respective uses. Similarly to the registration pointer of FIGS. 1 to 4, the registration pointer 60 has a detectable device base 64 for supporting detectable devices such that the registration pointer 60 can be tracked in space for position and orientation.

Referring to FIG. 10, a registration pointer in accordance with another embodiment of the present invention is illustrated at 70. The registration pointer 70 is provided with a base body 71 having a handle portion 72, a detectable device base 73, and a stem portion 74, all of which are generally similar in construction to the registration pointer 10 described previously. An end 75 of the stem portion 74 is used as a coupling portion, rather than a tip configuration. The embodiment illustrated in FIG. 10 has a male connector and threading, and bit-type tip configurations 76 and 77, consisting of removable tips of specified uses, can be screwingly coupled to the base body 71. Therefore, the tip configurations are interchanged according to the type of surface to register. Obviously, other types of tip configurations can be provided. It is also contemplated to provide the base body 71 with a socket end, and the bit-type tip configurations with snap-fit ends for the quick coupling of the tip configurations to the base body 71.

Returning to the embodiment of the registration pointer 10 of FIGS. 1 to 5, other removable tips could be provided, as alternatives to the above-described removable tip 50 (FIG. 5). For instance, a pointed tip adapted to perforate the soft tissue, a removable tip having a graduated surface to indicate the depth of insertion of the registration pointer, and other similar tip configurations are contemplated. It is pointed out that for inventory purposes, it is preferred to keep one registration pointer having interchangeable tips, e.g., the above described embodiments, than a plurality of registration pointers. Also, sterilization is also simplified by providing a plurality of tips rather than a plurality of complete registration pointers.

Figure 7:
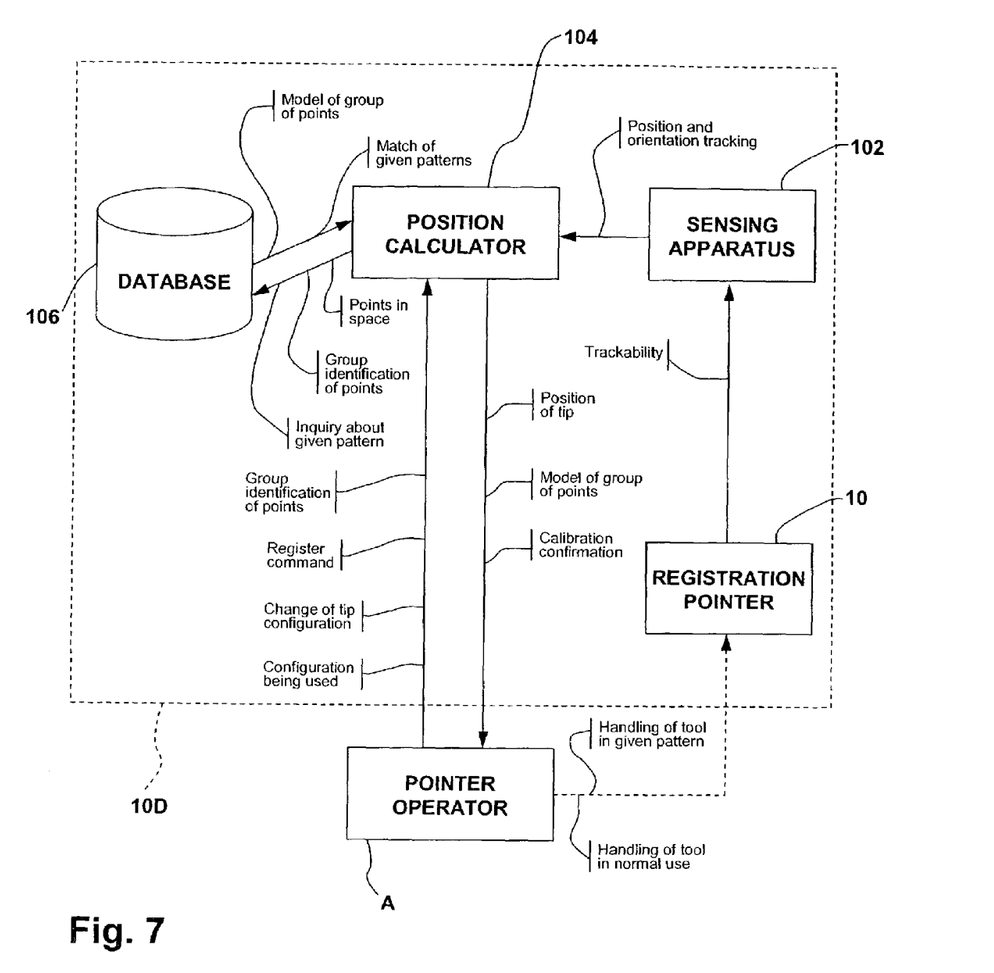
FIG. 7 is a block diagram of a computer-assisted surgery system having the registration pointer of the present invention.

Referring to FIG. 7, a CAS system in accordance with the present invention is generally shown at 100. The CAS system 100 has the registration pointer 10, a sensing apparatus 102, a position calculator 104 and a database 106. The position calculator 104 is connected to the sensing apparatus 102 and to the database 106. A pointer operator A (e.g., a surgeon) is illustrated interacting with the position calculator 104 and handling the registration pointer 10.

The sensing apparatus 102 is provided for tracking the registration pointer 10. More precisely, the sensing apparatus 102 is compatible with the detectable devices 35 on the registration pointer 10. In a preferred embodiment of the present invention, the detectable devices are passive (such as the retro-reflective spheres 35). An optical tracking system, such as Polaris™ by Northern Digital Inc., is well suited for being used as the sensing apparatus 102. Other types of tracking systems can be involved, and not necessarily passive ones. Active tracking systems, including electromagnetic devices or sound emitters, are contemplated as being suitable for the present invention.

Therefore, as illustrated in FIG. 7, the registration pointer 10 is tracked for position and orientation by the sensing apparatus 102.

A position of the tips of the tip configurations is determinable by calibration, whereby a position of the tip is calculable as a function of the tracking for position and orientation of the detectable device on the registration pointer 10. Accordingly, the position and orientation tracking performed by the sensing apparatus 102 is forwarded in real time to the position calculator 104, which calculates a position of the tip of the registration pointer 10. It is pointed out that the position calculator 104 must know the tip configuration being used on the registration pointer 10.

The position calculator 104 is typically a PC station, having a CPU, RAM and operator interfaces, such as a display unit, keyboard, mouse, foot pedal, etc. The database 106 is typically part of the PC station as the hard disk drive, and is used to store the points registered by the CAS system 100. The position calculator 104 performs the calculation of the position of the tip as a function of the position and orientation tracking by the sensing apparatus 102 and of the tip configuration being used.

The tip configuration being used can be indicated by the pointer operator A, for instance, using the operator interfaces. Once the tip configuration is known by the position calculator 104, the position of the tip of the registration pointer 10 can be calculated.

Now that the, CAS system 100 has been described, a method for using the registration pointer 10 will be disclosed.

Figure 8:
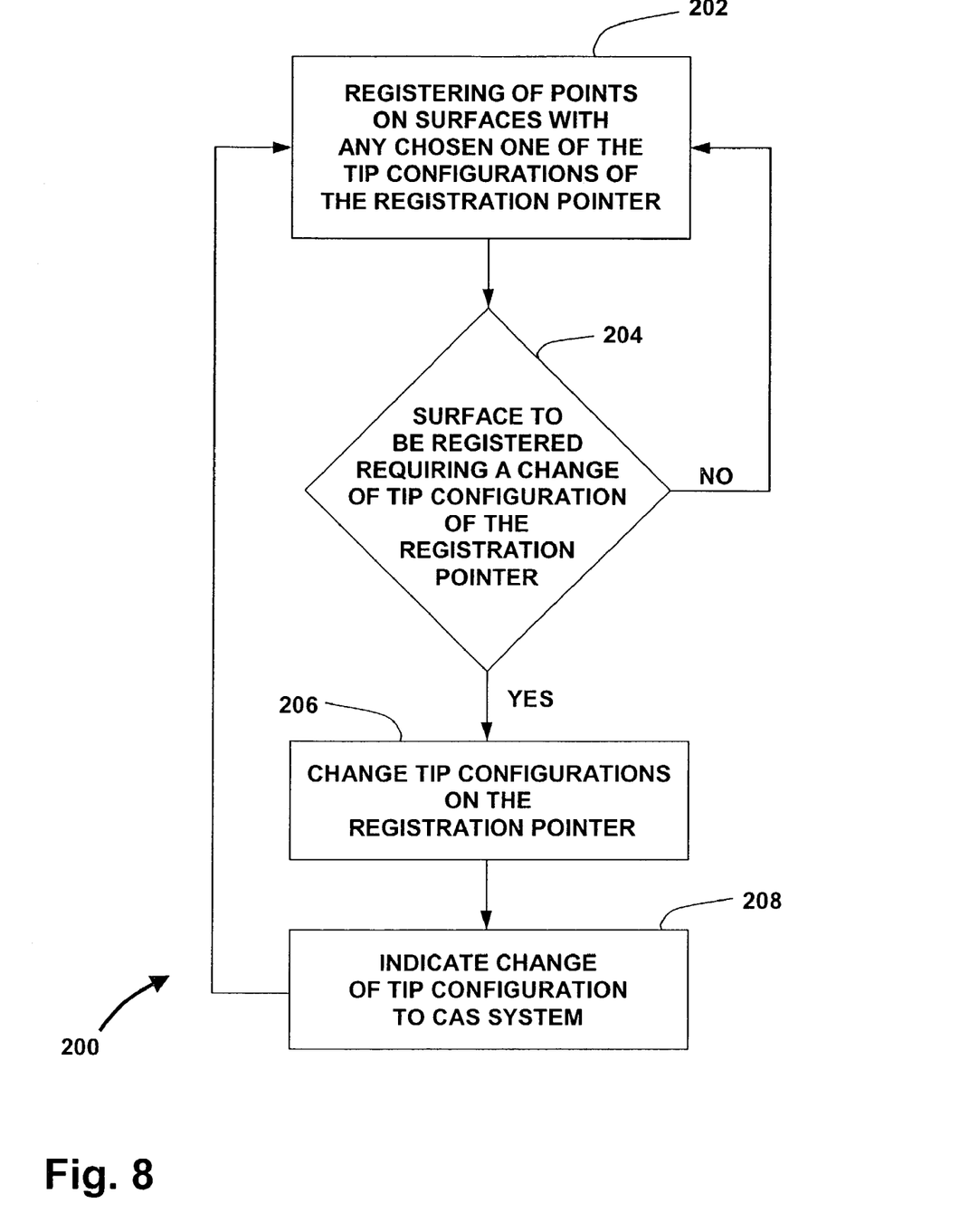
FIG. 8 is a flow chart of a method for registering points in accordance with the present invention.

Referring to FIG. 8, a method for registering points is generally shown at 200. Prior to proceeding with the method 200, the tip configurations of the registration pointer 10 are preferably calibrated. A new tip configuration can be calibrated following a change of tip configuration, but it is preferred that all calibration be performed previously (e.g., preoperatively). Calibration can be effected using a calibration base, as discussed in International Publication No. WO 01/67979 A1, by Jutras et al., as published on Sep. 20, 2001. It is pointed out that the geometry of the registration pointer 10 could be known by the CAS system 100 such that, once a first tip configuration is calibrated, the position calculator 104 can automatically calibrate the other tip configurations, considering that the tip configurations are in a fixed relative geometry with respect to one another. In such a case, the database 106 is used to store the fixed relative geometry, such that the fixed geometry can be retrieved by the position calculator 104.

Step 202 consists in registering points on a first surface. This is achieved with the registration pointer 10. Referring to FIG. 7, the pointer operator A (FIG. 7) touches a surface to be digitized with the registration pointer 10 in a given tip configuration. A register command is given by the pointer operator A to the position calculator 104. Upon receiving the register command, the position calculator 104 records the position of the tip (i.e., where the pointer 10 contacts the surface to register), as calculated from the position and orientation of the registration pointer 10 provided by the sensing apparatus 102. The registered point (i.e., the position of the tip) is stored in the database 106 by the position calculator 104 with a group identification. For instance, the group identification can be the bone that has been registered (e.g., points on the surface of the femoral head). Therefore, the pointer operator A can retrieve a group of points under a group identification. For instance, a 3-D model of the femoral head can be displayed to represent the points of a group identification.

Once a surface has been registered and another surface requires to be registered, the pointer operator A must decide whether the tip configuration being used on the registration pointer 10 is appropriate. Decision 204 consists in deciding whether to change tip configurations. If not, the new surface can be registered with the registration pointer 10 in the unchanged tip configuration, pursuant to Step 202.

If so, the tip configurations are changed on the registration pointer 10 pursuant to Step 206. According to the type of registration pointer being used, the change may require manual steps. The preferred embodiment of the present invention, i.e., the registration pointer 10 of FIGS. 1 to 4, requires that the removable tip 50 be either screwed onto the stem portion 40, or removed therefrom.

Step 208 consists in indicating a change of tip configuration to the CAS system 100. This can be achieved in a number of ways. As shown in FIG. 7, the pointer operator A can indicate a change of tip configuration to the position calculator 104 through the interfaces. Another contemplated way to indicate a change of tip configuration is to perform a given predetermined pattern with the registration pointer 10 having changed tip configuration. For instance, the pointer operator A can create a rotating motion about the tip configuration. The database 106 would be provided with the given predetermined patterns so as to provide the stored patterns to the position calculator 104 for comparison with the position and orientation tracking provided by the sensing apparatus 102. A calibration confirmation would then be displayed to the pointer operator A to indicate that the given predetermined pattern has been recognized and that the change of tip configuration is effective. Once the change of tip configuration has been recognized, the method 200 returns to Step 202 of registering points, but this time on the new surface with the changed tip configuration.

The registration pointer 10 is preferably used in combination with a trackable reference secured to a bone. The trackable reference is typically used as a frame of reference such that points registered by the registration pointer 10 can be related to a fixed reference on the bone. However, uses of the registration pointer 10 without a trackable reference are also contemplated. For instance, a bone can be fixed such that it is immovable. In such a case, a trackable reference is not required.

We claim:

1. A registration pointer for registering points of surfaces of bodily elements in computer-assisted surgery, comprising:

a handle for being manipulated by a pointer operator;

a stem connected to the handle;

a first tip configuration at a first tip of the stem;

a second tip configuration being a removable hollow stem portion that selectively matingly covers the first tip and a portion of the stem, with each tip configuration having a respective use relating to a registration of points on specified bodily elements; and a detectable device secured to any one of the handle, the stem and the tip configurations, the detectable device being adapted to be tracked in space for position and orientation by a sensing apparatus;

whereby a position of any one of the tip configurations with respect to the detectable device is determinable such that a position of any one of the tip configurations is calculable as a function of the position and orientation of the detectable device, any one of the tip configurations being chosen to register points on given bodily elements as a function of the respective use, by recording a position of points of contact between any one of the tip configurations and the given bodily element.

2. The registration pointer according to claim 1, wherein the hollow stem portion has a tapping portion, and the stem has a corresponding threading portion for detachable threading engagement with the tapping portion.

3. The registration pointer according to claim 1, wherein the stem has an intermediate portion of circular cross-section with a given diameter connected to the handle, and an end portion having the first tip, the end portion having a circular cross-section with a smaller diameter than said given diameter.

4. The registration pointer according to claim 3, wherein the hollow stem portion has an annular cross-section with an outer diameter equal to the given diameter such that stem and the hollow stem portion form a continuous smooth surface when secured to one another.

5. The registration pointer according to claim 1, wherein the first tip configuration has a blunt tip and the second tip configuration has a pointed tip, the respective use of the first tip configuration being to register points on a bone element following displacement of the blunt tip through soft tissue to reach the bone element, so as to substantially limit damage to the soft tissue, and the respective use of the second tip configuration being to register points on thin soft tissue covering bone element.

6. The registration pointer according to claim 1, wherein the detectable device is passive.

7. The registration pointer according to claim 6, wherein the detectable device has three retro-reflective spheres in a determined pattern.

8. The registration pointer according to claim 1, the number of the at least one stem is two, the first tip configuration being at an end of a first one of the stems, and the second tip configuration being at an end of a second one of the stems.

9. The registration pointer according to claim 1, wherein the tip configurations are bits releasably coupled to the stem of the registration pointer.

10. The registration pointer according to claim 9, wherein the tip configurations are screwingly engaged to the stem.

11. A method for registering, points on surfaces of bodily elements in computer-assisted surgery, comprising the steps of:
   i) providing a registration pointer with at least a first and a second tip configurations each having a respective use relating to a registration of points on specified bodily elements, and being trackable in space for position and orientation;
   ii) calibrating the registration pointer such that a position in space of any one of the tip configurations is calculable by a position calculator as a function of the tracking for position and orientation of the registration pointer;
   iii) regidtering points on a surface of a first bodily element with the first tip configuration by recording a position of points of contact between the first tip configuration and the surface of the first bodily element;
   iv) changing the use of the registration pointer from the first tip configuration to the second tip configuration;
   v) indicating to the position calculator a change of use from the first tip configuration to the second tip configuration for the registration pointer; and
   vi) registering points on a surface of a second bodily element with the second tip configuration by recording a position of points of contact between the second tip configuration and the surface of the second bodily element.

12. The method according to claim 11, wherein step ii) is performed by one of interacting with the position calibration, and displacing the registration pointer in a predetermined pattern recognizable by the position calculator.

13. The method according to claim 11, wherein steps iii) and v) are repeated for subsequent changes of the tip configuration used on the registration pointer.

14. The method according to claim 11, wherein the respective use of the first tip configuration is to register points on a bone element following displacement of the second tip configuration through soft tissue to reach the bone element, so as to substantially limit damage to the soft tissue, and the respective use of the second tip configuration is to register points on thin soft tissue covering bone element.

15. The method according to claim 11, wherein the tip configurations have a relative fixed geometry with respect to one another, such that a position of an uncalibrated one of the tip configurations is calculable as a function of a position of a calibrated one of the tip configurations in step ii).

* * * * *